(12) United States Patent
Stempfer et al.

(10) Patent No.: US 6,936,455 B1
(45) Date of Patent: Aug. 30, 2005

(54) PRODUCTION OF HETEROLOGOUS PROTEINS USING AN $N^{PRO}$ AUTOPROTEASE OF A PESTIVIRUS AND INCLUSION BODIES

(75) Inventors: Günter Stempfer, Kramsach (AT); Jörg Windisch, Kramsach (AT); Franz Knauseder, Kirchbichl (AT)

(73) Assignee: Sandoz AG, Basel (CH)

( * ) Notice: Subject to any disclaimer, the term of this patent is extended or adjusted under 35 U.S.C. 154(b) by 38 days.

(21) Appl. No.: 10/048,882

(22) PCT Filed: Aug. 7, 2000

(86) PCT No.: PCT/EP00/07643

§ 371 (c)(1),
(2), (4) Date: Sep. 17, 2002

(87) PCT Pub. No.: WO01/11057

PCT Pub. Date: Feb. 15, 2001

(30) Foreign Application Priority Data

Aug. 9, 1999 (AT) .............................. 1367/99

(51) Int. Cl.[7] .......................... C12N 9/48; C12N 1/20; C12P 21/06; C12Q 1/70; C07K 1/00
(52) U.S. Cl. .................... 435/212; 435/69.1; 435/69.7; 435/252.33; 435/5; 530/300; 530/355; 530/412
(58) Field of Search .............................. 435/212, 69.1, 435/69.7, 252.33, 5; 530/300, 355, 412, 324, 350, 351, 344, 402; 536/23.1, 23.4

(56) References Cited

U.S. PATENT DOCUMENTS 5,149,783 A   9/1992   Sommergruber et al.

FOREIGN PATENT DOCUMENTS

| CA | 2301698 | 3/1999 |
| EP | 234888 | 9/1987 |
| EP | 321973 | 6/1989 |
| WO | WO 98/49326 | 5/1998 |
| WO | WO 99/10483 | 3/1999 |
| WO | WO 99/10503 | 3/1999 |

OTHER PUBLICATIONS

Collins–Racie et al., Bio–Technology, vol. 13, No. 9, 982–987 (1995).
Muyldermans et al., Virus Genes, vol. 13, No. 2, 135–142 (1996).
Ruemenapf et al., J of Virology, vol. 72, No. 3, 2544–2547 (1998).
Stark et al., J. of Virology, vol. 67, No. 12, 7088–7095 (1993).
Wiskerchen et al., J. of Virology, vol. 65, No. 8, 4508–4514 (1991).
Bachmann, "Section G. Strains and Useful Strain Constructions, 72. Derivations and Genotypes of Some Mutant Derivatives of *Escherichia coli* K–12", *Escherichia coli and Salmonella Typhimurium: Cellular and Molecular Biology*, vol. 2, Neidhardt, Ed., American Society for Microbiology, Washington, DC, pp. 1190–1219 (1987).
Bachmann, "Section A. The Genome, 53. Linkage Map of *Escherichia coli* K–12, Edition 7", *Escherichia coli and Salmonella Typhimurium: Cellular and Molecular Biology*, vol. 2, Neidhardt, Ed., American Society for Microbiology, Washington, DC, pp. 807–876 (1987).
Jensen, "The *Escherichia coli* K–12 'Wild Types' W3110 and MG1655 Have an rph Frameshift Mutation That Leads to Pyrimidine Starvation Due to Low pyrE Expression Levels", *J Bacteriol*, vol. 175, No. 11, pp. 3401–3407 (1993).
Rudolph, "Renaturation of Recombinant, Disulfide–Bonded Proteins from 'Inclusion Bodies'", *Modern Methods in Protein–and Nucleic Acid Research*, Tschesche, Ed., pp. 149–171 (1990).
Rudolph, "Chapter 10: Successful Protein Folding on an Industrial Scale", *Protein Engineering: Principles and Practice*, Cleland and Craik, Eds., John Wiley & Sons, Inc., pp. 283–298 (1996).
Rudolph, Bohm, Lilie and Jaenicke, "3: Folding Proteins", *Protein Function. A Practical Approach*, Second Edition, Creighton, Ed., pp. 57–99 (1997).
Varnavski and Khromykh, "Noncytopathic Flavivirus Replicon RNA–Based System for Expression and Delivery of Heterologous Genes", *Virology*, vol. 255, No. 2, pp. 366–375 (1999).
Knippers, Rolf, Molekulare Genetic, 6th Edition, Georg Thieme Verlag, Stuttgart, New York (Monograph) (1995).
Studier, F.W., Methods in Enzymology 185, pp. 60–89 (1990).
Abstract of oral presentation No. 4 V2 at the Jahrestagung Gesellschaft für Virologie, Hamburg, Oct. 13, 2003 (1997).
Poster Abstract No. 7P33 at the Jahrestagung Gesellschaft für Virologie, Regensburg, Mar. 2, 2005., (1998).
Poster Abstract No. P2–46 at the Fifth International Symposium on Positive Strand RNA Viruses, St. Petersburg, Florida, May 23–28 (1998).
E. F. Rossomando, Methods in Enzymology, vol. 182: Guide to Protein Purification, Academic Press Inc., pp. 309–392 (1990).

*Primary Examiner*—Gerry Leffers
*Assistant Examiner*—Maria Marvich
(74) *Attorney, Agent, or Firm*—John D. Thallemer; Diane E. Furman

(57) ABSTRACT

The present invention relates to a process for the recombinant production of a desired heterologous polypeptide with a clearly defined homogenous N-terminus in a bacteria host cell. A fusion comprising a peptide with the autoproteolytic activity of an autoprotease $N^{pro}$ of a pestivirus and the heterologous polypeptide is initially expressed in the form of cytoplasmic inclusion bodies in the host cell, the inclusion bodies are isolated and subsequently treated so that the desired heterologous polypeptide is cleaved autoproteolytically by the $N^{pro}$ activity of the fusion protein.

9 Claims, No Drawings

SEQUENCE LISTING

<160> NUMBER OF SEQ ID NOS: 13

<210> SEQ ID NO 1
<211> LENGTH: 168
<212> TYPE: PRT
<213> ORGANISM: Pestivirus sp.

<400> SEQUENCE: 1

Met Glu Leu Asn His Phe Glu Leu Leu Tyr Lys Thr Ser Lys Gln Lys
 1               5                  10                  15

Pro Val Gly Val Glu Glu Pro Val Tyr Asp Thr Ala Gly Arg Pro Leu
             20                  25                  30

Phe Gly Asn Pro Ser Glu Val His Pro Gln Ser Thr Leu Lys Leu Pro
         35                  40                  45

His Asp Arg Gly Arg Gly Asp Ile Arg Thr Thr Leu Arg Asp Leu Pro
     50                  55                  60

Arg Lys Gly Asp Cys Arg Ser Gly Asn His Leu Gly Pro Val Ser Gly
 65                  70                  75                  80

Ile Tyr Ile Lys Pro Gly Pro Val Tyr Tyr Gln Asp Tyr Thr Gly Pro
                 85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 2
<211> LENGTH: 16
<212> TYPE: PRT
<213> ORGANISM: Pestivirus sp.

```
<400> SEQUENCE: 2

Met Glu Leu Asn His Phe Glu Leu Leu Tyr Lys Thr Ser Lys Gln Lys
 1               5                  10                  15

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:
      Oligo-histidine purification aid

<400> SEQUENCE: 3

Met Ala Ser His His His His His His
 1               5                  10

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide comprising sequence derived from human growth
      hormone cDNA

<400> SEQUENCE: 4
ataattacta gttgtttccc aaccattccc ttatccaggc c                 41

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide comprising sequence derived from human growth
      hormone cDNA

<400> SEQUENCE: 5
ataattggat cctcgagtta ttagaagcca cagctgccct ccac              44

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide comprising sequence derived from human growth
      hormone cDNA

<400> SEQUENCE: 6
agggtatcta gaattctatg ccagtgggag tggaggaacc g                 41

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide comprising sequence derived from human growth
      hormone cDNA

<400> SEQUENCE: 7
agaattaagc ttctagatta ttagaagcca cagctgccct ccac              44

<210> SEQ ID NO 8
<211> LENGTH: 1072
```

<212> TYPE: DNA
<213> ORGANISM: Artificial Sequence
<220> FEATURE:
<223> OTHER INFORMATION: Description of Artificial Sequence:Sequence of
      Pestivirus combined with sequence of Homo sapiens

<400> SEQUENCE: 8

```
agggtatcta gaattctatg ccagtgggag tggaggaacc ggtgtatgac accgcgggga      60
gaccactatt tgggaaccca agtgaggtac acccacaatc aacgctgaag ctgccacacg     120
acagggggag aggagatatc agaacaacac tgagggacct acccaggaaa ggtgactgta     180
ggagtggcaa ccatctaggc ccggttagtg ggatatacat aaagcccggc cctgtctact     240
atcaggacta cacgggccca gtctatcaca gagctccttt agagttcttt gatgaggccc     300
agttctgcga ggtgactaag agaataggca gggtcacggg tagtgatggt aagctttacc     360
acatatatgt gtgcgtcgat ggttgcatac tgctgaaatt agccaaaagg ggcacaccca     420
gaaccctaaa gtggattagg aacttcacca actgtccatt atgggtaact agttgtttcc     480
caaccattcc cttatccagg ccttttgaca acgctatgct ccgcgcccat cgtctgcacc     540
agctggcctt tgacacctac caggagtttg aagaagccta tcccaaag gaacagaagt       600
attcattcct gcagaacccc cagacctccc tctgtttctc agagtctatt ccgacaccct     660
ccaacaggga ggaaacacaa cagaaatcca acctagagct gctccgcatc tccctgctgc     720
tcatccagtc gtggctggag cccgtgcagt tcctcaggag tgtcttcgcc aacagcctgg     780
tgtacggcgc tctgacagc aacgtctatg acctcctaaa ggacctagag gaaggcatcc      840
aaacgctgat ggggaggctg gaagatggca gcccccggac tgggcagatc ttcaagcaga     900
cctacagcaa gttcgacaca aactcacaca acgatgacgc actactcaag aactacgggc     960
tgctctactg cttcaggaag gacatggaca aggtcgagac attcctgcgc atcgtgcagt    1020
gccgctctgt ggagggcagc tgtggcttct aataatctag aagcttaatt ct            1072
```

<210> SEQ ID NO 9
<211> LENGTH: 344
<212> TYPE: PRT
<213> ORGANISM: Artificial Sequence
<220> FEATURE:
<223> OTHER INFORMATION: Description of Artificial Sequence:Sequence of
      Pestivirus combined with sequence of Homo sapiens

<400> SEQUENCE: 9

```
Met Pro Val Gly Val Glu Glu Pro Val Tyr Asp Thr Ala Gly Arg Pro
  1               5                  10                  15

Leu Phe Gly Asn Pro Ser Glu Val His Pro Gln Ser Thr Leu Lys Leu
                 20                  25                  30

Pro His Asp Arg Gly Arg Gly Asp Ile Arg Thr Thr Leu Arg Asp Leu
             35                  40                  45

Pro Arg Lys Gly Asp Cys Arg Ser Gly Asn His Leu Gly Pro Val Ser
         50                  55                  60

Gly Ile Tyr Ile Lys Pro Gly Pro Val Tyr Tyr Gln Asp Tyr Thr Gly
 65                  70                  75                  80

Pro Val Tyr His Arg Ala Pro Leu Glu Phe Phe Asp Glu Ala Gln Phe
                 85                  90                  95

Cys Glu Val Thr Lys Arg Ile Gly Arg Val Thr Gly Ser Asp Gly Lys
                100                 105                 110

Leu Tyr His Ile Tyr Val Cys Val Asp Gly Cys Ile Leu Leu Lys Leu
            115                 120                 125
```

-continued

| | | | | | | | | | | | | |
|---|---|---|---|---|---|---|---|---|---|---|---|---|
|Ala|Lys|Arg|Gly|Thr|Pro|Arg|Thr|Leu|Lys|Trp|Ile|Arg|Asn|Phe|Thr|
|130| | | | |135| | | | |140| | | | | |

Asn Cys Pro Leu Trp Val Thr Ser Cys Phe Pro Thr Ile Pro Leu Ser
145                 150                 155                 160

Arg Pro Phe Asp Asn Ala Met Leu Arg Ala His Arg Leu His Gln Leu
                165                 170                 175

Ala Phe Asp Thr Tyr Gln Glu Phe Glu Glu Ala Tyr Ile Pro Lys Glu
            180                 185                 190

Gln Lys Tyr Ser Phe Leu Gln Asn Pro Gln Thr Ser Leu Cys Phe Ser
        195                 200                 205

Glu Ser Ile Pro Thr Pro Ser Asn Arg Glu Glu Thr Gln Gln Lys Ser
    210                 215                 220

Asn Leu Glu Leu Leu Arg Ile Ser Leu Leu Leu Ile Gln Ser Trp Leu
225                 230                 235                 240

Glu Pro Val Gln Phe Leu Arg Ser Val Phe Ala Asn Ser Leu Val Tyr
                245                 250                 255

Gly Ala Ser Asp Ser Asn Val Tyr Asp Leu Leu Lys Asp Leu Glu Glu
                260                 265                 270

Gly Ile Gln Thr Leu Met Gly Arg Leu Glu Asp Gly Ser Pro Arg Thr
            275                 280                 285

Gly Gln Ile Phe Lys Gln Thr Tyr Ser Lys Phe Asp Thr Asn Ser His
        290                 295                 300

Asn Asp Asp Ala Leu Leu Lys Asn Tyr Gly Leu Leu Tyr Cys Phe Arg
305                 310                 315                 320

Lys Asp Met Asp Lys Val Glu Thr Phe Leu Arg Ile Val Gln Cys Arg
                325                 330                 335

Ser Val Glu Gly Ser Cys Gly Phe
            340

<210> SEQ ID NO 10
<211> LENGTH: 4840
<212> TYPE: DNA
<213> ORGANISM: Artificial Sequence
<220> FEATURE:
<223> OTHER INFORMATION: Description of Artificial Sequence:Sequence of
      expression plasmid comprising sequence of
      Pestivirus and sequence of Homo sapiens

<400> SEQUENCE: 10

```
gaattctcat gtttgacagc ttatcatcga taagctttaa tgcggtagtt tatcacagtt     60
aaattgctaa cgcagtcagg caccgtgtat gaaatctaac aatgcgctca tcgtcatcct    120
cggcaccgtc accctggatg ctgtaggcat aggcttggtt atgccggtac tgccgggcct    180
cttgcgggat atcgtccatt ccgacagcat cgccagtcac tatggcgtgc tgctagcgct    240
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcctctacgc cggacgcatc gtggccggca tcaccggcgc    420
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt gcggcggcgg tgctcaacgg    600
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
```

-continued

```
gctctgggtc attttcggcg aggaccgctt tcgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
agaattggag ccaatcaatt cttgcggaga actgtgaatg cgcaaaccaa cccttggcag   1380
aacatatcca tcgcgtccgc catctccagc agccgcacgc ggcgcatctc gggcagcgtt   1440
gggtcctggc cacgggtgcg catgatcgtg ctcctgtcgt tgaggacccg gctaggctgg   1500
cggggttgcc ttactggtta gcagaatgaa tcaccgatac gcgagcgaac gtgaagcgac   1560
tgctgctgca aaacgtctgc gacctgagca acaacatgaa tggtcttcgg tttccgtgtt   1620
tcgtaaagtc tggaaacgcg gaagtcagcc cctgcacca ttatgttccg gatctgcatc   1680
gcaggatgct gctggctacc ctgtggaaca cctacatctg tattaacgaa gcgctggcat   1740
tgaccctgag tgattttttct ctggtcccgc cgcatccata ccgccagttg tttaccctca   1800
caacgttcca gtaaccgggc atgttcatca tcagtaaccc gtatcgtgag catcctctct   1860
cgtttcatcg gtatcattac ccccatgaac agaaattccc ccttacacgg aggcatcaag   1920
tgaccaaaca ggaaaaaacc gcccttaaca tggcccgctt tatcagaagc cagacattaa   1980
cgcttctgga gaaactcaac gagctggacg cggatgaaca ggcagacatc tgtgaatcgc   2040
ttcacgacca cgctgatgag ctttaccgca gctgcctcgc gcgtttcggt gatgacggtg   2100
aaaacctctg acacatgcag ctcccggaga cggtcacagc ttgtctgtaa gcggatgccg   2160
ggagcagaca agcccgtcag ggcgcgtcag cgggtgttgg cgggtgtcgg ggcgcagcca   2220
tgacccagtc acgtagcgat agcggagtgt atactggctt aactatgcgg catcagagca   2280
gattgtactg agagtgcacc atatgcggtg tgaaataccg cacagatgcg taaggagaaa   2340
ataccgcatc aggcgctctt ccgcttcctc gctcactgac tcgctgcgct cggtcgttcg   2400
gctgcggcga gcggtatcag ctcactcaaa ggcggtaata cggttatcca cagaatcagg   2460
ggataacgca ggaaagaaca tgtgagcaaa aggccagcaa aaggccagga accgtaaaaa   2520
ggccgcgttg ctggcgtttt tccataggct ccgcccccct gacgagcatc acaaaaatcg   2580
acgctcaagt cagaggtggc gaaacccgac aggactataa agataccagg cgtttccccc   2640
tggaagctcc ctcgtgcgct ctcctgttcc gaccctgccg cttaccggat acctgtccgc   2700
ctttctccct tcgggaagcg tggcgctttc tcatagctca cgctgtaggt atctcagttc   2760
ggtgtaggtc gttcgctcca agctgggctg tgtgcacgaa ccccccgttc agcccgaccg   2820
ctgcgcctta tccggtaact atcgtcttga gtccaacccg gtaagacacg acttatcgcc   2880
actggcagca gccactggta acaggattag cagagcgagg tatgtaggcg gtgctacaga   2940
gttcttgaag tggtggccta actacggcta cactagaagg acagtatttg gtatctgcgc   3000
tctgctgaag ccagttacct tcggaaaaag agttggtagc tcttgatccg gcaaacaaac   3060
caccgctggt agcggtggtt ttttgtttg caagcagcag attacgcgca gaaaaaaagg   3120
```

```
atctcaagaa gatcctttga tcttttctac ggggtctgac gctcagtgga acgaaaactc      3180
acgttaaggg atttttggtca tgagattatc aaaaaggatc ttcacctaga tcctttaaa      3240 ttaaaaatga agttttaaat caatctaaag tatatatgag taaacttggt ctgacagtta      3300
cctcgaggcc atccgtcagg atggccttct gcttaatttg atgcctggca gtttatggcg      3360
ggcgtcctgc ccgccaccct ccgggccgtt gcttcgcaac gttcaaatcc gctcccggcg      3420
gatttgtcct actcaggaga gcgttcaccg acaaacaaca gataaaacga aaggcccagt      3480 cttttcgactg agcctttcgt tttattctag attattagaa gccacagctg ccctccacag      3540
agcggcactg cacgatgcgc aggaatgtct cgaccttgtc catgtccttc ctgaagcagt      3600
agagcagccc gtagttcttg agtagtgcgt catcgttgtg tgagtttgtg tcgaacttgc      3660
tgtaggtctg cttgaagatc tgcccagtcc ggggctgcc atcttccagc ctccccatca      3720
gcgtttggat gccttcctct aggtccttta ggaggtcata gacgttgctg tcagaggcgc      3780
cgtacaccag gctgttggcg aagacactcc tgaggaactg cacgggctcc agccacgact      3840
ggatgagcag cagggagatg cggagcagct ctaggttgga tttctgttgt gtttcctccc      3900
tgttggaggg tgtcggaata gactctgaga aacagaggga ggtctggggg ttctgcagga      3960
atgaatactt ctgttccttt gggatatagg cttcttcaaa ctcctggtag gtgtcaaagg      4020
ccagctggtg cagacgatgg gcgcggagca tagcgttgtc aaaaggcctg gataagggaa      4080
tggttgggaa acaactagtt acccataatg gacagttggt gaagttccta atccacttta      4140
gggttctggg tgtgccccTt ttggctaatt tcagcagtat gcaaccatcg acgcacacat      4200
atatgtggta aagcttacca tcactacccg tgaccctgcc tattctctta gtcacctcgc      4260
agaactgggc ctcatcaaag aactctaaag gagctctgtg atagactggg cccgtgtagt      4320
cctgatagta gacagggccg ggctttatgt atatcccact aaccgggcct agatggttgc      4380
cactcctaca gtcacctttc ctgggtaggt ccctcagtgt tgttctgata tctcctctcc      4440
ccctgtcgtg tggcagcttc agcgttgatt gtgggtgtac ctcacttggg ttcccaaata      4500
gtggtctccc cgcggtgtca taccggtt cctccactcc cactggcata gaattctaga      4560 taccttttt acgtgaactt gcgtactagt taactagttc gatgattaat tgtcaacagc      4620
tcatttcaga atatttgcca gaaccgttat gatgtcggcg caaaaaacat tatccagaac      4680
gggagtgcgc cttgagcgac acgaattatg cagtgattta cgacctgcac agccatacca      4740
cagcttccga ttggctgcct gacgccagaa gcattggtgc accgtgcagt cgagatgcgc      4800
gtcggcaccc tggcgatcac cgaccatgac accacagcat                            4840
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11 tcccagcca tgcccttgtc c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
gaaggcacag ctgctctcca c                                            21

<210> SEQ ID NO 13
<211> LENGTH: 342
<212> TYPE: PRT
<213> ORGANISM: Artificial Sequence
<220> FEATURE:
<223> OTHER INFORMATION: Description of Artificial Sequence:Sequence of
      Pestivirus combined with porcine sequence

<400> SEQUENCE: 13

```
Met Pro Val Gly Val Glu Glu Pro Val Tyr Asp Thr Ala Gly Arg Pro
  1               5                  10                  15

Leu Phe Gly Asn Pro Ser Glu Val His Pro Gln Ser Thr Leu Lys Leu
             20                  25                  30

Pro His Asp Arg Gly Arg Gly Asp Ile Arg Thr Thr Leu Arg Asp Leu
         35                  40                  45

Pro Arg Lys Gly Asp Cys Arg Ser Gly Asn His Leu Gly Pro Val Ser
     50                  55                  60

Gly Ile Tyr Ile Lys Pro Gly Pro Val Tyr Tyr Gln Asp Tyr Thr Gly
 65                  70                  75                  80

Pro Val Tyr His Arg Ala Pro Leu Glu Phe Phe Asp Glu Ala Gln Phe
                 85                  90                  95

Cys Glu Val Thr Lys Arg Ile Gly Arg Val Thr Gly Ser Asp Gly Lys
            100                 105                 110

Leu Tyr His Ile Tyr Val Cys Val Asp Gly Cys Ile Leu Leu Lys Leu
            115                 120                 125

Ala Lys Arg Gly Thr Pro Arg Thr Leu Lys Trp Ile Arg Asn Phe Thr
130                 135                 140

Asn Cys Pro Leu Trp Val Thr Ser Cys Phe Pro Ala Met Pro Leu Ser
145                 150                 155                 160

Ser Leu Phe Ala Asn Ala Val Leu Arg Ala Gln His Leu His Gln Leu
                165                 170                 175

Ala Ala Asp Thr Tyr Lys Glu Phe Glu Arg Ala Tyr Ile Pro Glu Gly
            180                 185                 190

Gln Arg Tyr Ser Ile Gln Asn Ala Gln Ala Ala Phe Cys Phe Ser Glu
            195                 200                 205

Thr Ile Pro Ala Pro Thr Gly Lys Asp Glu Ala Gln Gln Arg Ser Val
    210                 215                 220

Glu Leu Leu Arg Phe Ser Leu Leu Leu Ile Gln Ser Trp Leu Gly Pro
225                 230                 235                 240

Val Gln Phe Leu Ser Arg Val Phe Thr Asn Ser Leu Val Phe Gly Thr
                245                 250                 255

Ser Asp Arg Val Tyr Glu Lys Leu Lys Asp Leu Glu Glu Gly Ile Gln
            260                 265                 270

Ala Leu Met Arg Glu Leu Glu Asp Gly Ser Pro Arg Ala Gly Gln Ile
            275                 280                 285

Leu Lys Gln Thr Tyr Asp Lys Phe Asp Thr Asn Leu Arg Ser Asp Asp
    290                 295                 300

Ala Leu Leu Lys Asn Tyr Gly Leu Leu Ser Cys Phe Lys Lys Asp Leu
305                 310                 315                 320
```

```
His Lys Ala Glu Thr Tyr Leu Arg Val Met Lys Cys Arg Arg Phe Val
            325                 330                 335
Glu Ser Ser Cys Ala Phe
            340
```

PRODUCTION OF HETEROLOGOUS PROTEINS USING AN N^PRO AUTOPROTEASE OF A PESTIVIRUS AND INCLUSION BODIES

The present invention relates to a process for the recombinant production of a desired heterologous polypeptide with a clearly defined homogeneous N-terminus in a bacterial host cell, wherein initially a fusion protein which comprises a peptide having the autoproteolytic activity of an autoprotease $N^{pro}$ of a pestivirus and the heterologous polypeptide is produced in the form of cytoplasmic inclusion bodies in the host cell, and then the inclusion bodies are isolated and treated in such a way that the desired heterologous polypeptide is cleaved from the fusion protein by the $N^{pro}$ autoproteolytic activity.

In the production of recombinant proteins in heterologous organisms such as the expression of human or other eukaryotic proteins in bacterial cells it is often difficult to obtain a dearly defined N-terminus which is as nearly 100% homogeneous as possible. This applies in particular to recombinant pharmaceutical proteins whose amino acid sequence ought in many cases to be identical to the amino acid sequence naturally occurring in humans/animals.

On natural expression, for example in humans, many pharmaceutical proteins which are in use are transported into the extracellular space, and cleavage of the signal sequence present in the precursor protein for this purpose results in a clearly defined N-terminus. Such a homogenous N-terminus is not always easy to produce for example in bacterial cells for several reasons.

For production on an industrial scale, many pharmaceutical proteins are produced in the cytoplasm of bacterial cells (for example *Escherichia coli*) because accumulation thereof in adequate quantities is possible, and moreover insoluble inclusion bodies (IBs) are often formed which have great advantages in the working up and purification. In addition, the protein expressed in the form of IBs is protected from protease degradation by intracellular proteases (R. Rudolph, in: Protein Engineering: Principles and Practices. Eds. Jeffrey L. Cleland and Charles S. Craik, John Wiley & Sons Inc., (1995), ISBN 0-471-10354-3).

However, production of IB material requires in vitro refolding of the expressed protein. This can in many cases be effected by methods known per se (R. Rudolph et al. (1996), in:

Protein Function: A Practical Approach, Ed.: Creighton, T. E., 1–39). To do this, the proteins in the form of IBs are solubilized by adding strong denaturing agents under reducing conditions and are then renatured.

Only in rare cases is export into the bacterial periplasm with the aid of a pro- or eukaryotic signal sequence suitable, because it is usually possible to accumulate only very small quantities of product here because of the low transport capacity of the bacterial export machinery.

However, the bacterial cytoplasm differs considerably from the extracellular space of eukaryotes. On the one hand, reducing conditions are present therein and, on the other hand, there is no mechanism for cleaving N-terminal leader sequences to form mature proteins. The synthesis of all cytoplasmic proteins starts with a methionine which is specified by the appropriate start codon (ATG=initiation of translation). This N-terminal methionine is retained in many proteins, while in others it is cleaved by the methionine aminopeptidase (MAP) present in the cytoplasm and intrinsic to the host. The efficiency of the cleavage depends essentially on two parameters: 1. the nature of the following amino acid, and 2. the location of the N-terminus in the three-dimensional structure of the protein. The N-terminal methionine is preferentially deleted when the following amino acid is serine, alanine, glycine, methionine or valine and when the N-terminus is exposed, i.e. not "hidden" inside the protein. On the other hand, it the following amino acid is a different one, in particular a charged one (glutamic acid, aspartic acid, lysine, arginine), or if the N-terminus is located inside the protein, in most cases cleavage of the N-terminal methionine does not occur (Knippers, Rolf (1995) Molekulare Genetik., 6th edition, *Georg Thieme Verlag*. Stuttgart, New York. ISBN 3-13-103916-7).

And even if an amino acid promoting the cleavage is present at position 2, the cleavage is rarely complete. It is usual for a not inconsiderable proportion (1–50%) to remain unaffected by the MAP.

In the early days of the production of recombinant pharmaceutical proteins in bacterial cells the procedure was simply to put a methionine-encoding ATG start codon in front of the open reading frame (ORF) for the mature (i.e. without signal sequence or other N-terminal extension) protein. The expressed protein then had the sequence $H_2N$-Met-target protein.

Only in a few cases was it possible to achieve complete cleavage of the N-terminal methionine by the MAP intrinsic to the host. Most of the proteins produced in this way therefore either are inhomogeneous in relation to their N-terminus (mixture of Met form and Met-free form) or they all have an additional foreign amino acid (Met) at the N-terminus (only Met form).

This inhomogeneity or deviation from the natural sequence is, however, unacceptable in many cases because these products frequently show different immunological (for example induction of antibody formation) and pharmacological (half-life, pharmacokinetics) properties. For these reasons, it is now necessary in most cases to produce a nature-identical product (homogeneous and without foreign amino acids at the N-terminus). In the case of cytoplasmic expression, the remedy here in most cases is to fuse a cleavage sequence (leader) for a specific endopeptidase (for example factor Xa, enterokinase, KEX endopeptidases, IgA protease) or aminopeptidase (for example dipeptidyl aminopeptidase) to the N-terminus of the target protein. However, this makes an additional step, with expenditure of costs and materials, necessary during further working up, the so-called downstream processing, of the product. In addition, in the presence of IBs there is in many cases interference with or even complete prevention of the refolding by the leader sequence.

There is thus a need for a process for producing a desired heterologous target protein which is expressed in the form of inclusion bodies in bacterial cells, from which the target protein can then be prepared with a uniform, desired N-terminus. Such a process for producing a desired target protein from inclusion bodies using the viral autoprotease $N^{pro}$ from pestiviruses has been developed within the scope of the present invention.

Pestiviruses form a group of pathogens which cause serious economic losses in pigs and ruminants around the world. As the pathogen of a notifiable transmissible disease, the classical swine fever virus (CSFV) is particularly important. The losses caused by bovine viral diarrhoea virus (BVDV) are also considerable, especially through the regular occurrence of intrauterine infections of fetuses.

Pestiviruses are small enveloped viruses with a genome which acts directly as mRNA and is 12.3 kb in size and from which the viral gene products are transcribed in the cytoplasm.

This takes place in the form of a single polyprotein which comprises about 4000 amino acids and which is broken down both by viral and by cellular proteases into about 12 mature proteins.

To date, two virus-encoded proteases have been identified in pestiviruses, the autoprotease $N^{pro}$ and the serine protease NS3. The N-terminal protease $N^{pro}$ is located at the N-terminus of the polyprotein and has an apparent molecular mass of 23 kd. It catalyses a cleavage which takes place between its own C-terminus (Cys168) and the N-terminus (Ser169) of nucleocapsid protein C (R. Stark et al., J. Virol. 67 (1993), 7088–7095). In addition, duplications of the $N^{pro}$ gene have been described in cytopathogenic BVDV viruses. In these there is a second copy of $N^{pro}$ at the N-terminus of the likewise duplicated NS3 protease. An autoproteolytic cleavage of the $N^{pro}$-NS3 protein is observed in this case too (R. Stark et al., see above).

$N^{pro}$ is an autoprotease with a length of 168 amino acids and an apparent M, of about 20,000 d (in vivo). It is the first protein in the polyprotein of pestiviruses (CSFV, BDV (border disease virus) or BVDV) and undergoes autoproteolytic cleavage from the following nucleocapsid protein C (M. Wiskerchen et al., J. Virol. 65 (1991), 4508–4514; Stark et al., J. Virol. 67 (1993), 7088–7095). This cleavage takes place after the last amino acid in the sequence of $N^{pro}$, Cys168.

It has now surprisingly been found within the scope of the present invention that the autoproteolytic function of the autoprotease $N^{pro}$ can be utilized for cleaving a heterologous polypeptide from a fusion protein which is expressed in the form of inclusion bodies in a bacterial expression system and which comprises an autoprotease $N^{pro}$ of a pestivirus and the heterologous polypeptide. This entails uncleaved $N^{pro}$ fusion protein being isolated from inclusion bodies, solubilized and cleaved during refolding.

In one aspect, the present invention thus relates to a process for the recombinant production of a haterologous polypeptide, comprising
(i) cultivation of a bacterial host cell which is transformed with an expression vector which comprises a nucleic acid molecule which codes for a fusion protein, the fusion protein comprising a first polypeptide which exhibits the autoproteolytic function of an autoprotease $N^{pro}$ of a pestivirus, and a second polypeptide which is connected to the first polypeptide at the C-terminus of the first polypeptide in a manner such that the second polypeptide is capable of being cleaved from the fusion protein by the autoproteolytic activity of the first polypeptide, and the second polypeptide being a heterologous polypeptide, wherein cultivation occurs under conditions which cause expression of the fusion protein and formation of corresponding cytoplasmic inclusion bodies,
(ii) isolation of the inclusion bodies from the host cell,
(iii) solubilization of the isolated inclusion bodies,
(iv) dilution of the solubilizate to give a reaction solution in which the autoproteolytic cleavage of the heterologous polypeptide from the fusion protein is performed, and (v) isolation of the cleaved heterologous polypeptide.

A polypeptide with the autoproteolytic function of an autoprotease $N^{pro}$ of a pestivirus is, in particular, an autoprotease $N^{pro}$ of a pestivirus or a derivative thereof with autoproteolytic activity.

For the purpose of the present invention, the term "heterologous polypeptide" means a polypeptide which is not naturally cleaved by an autoprotease $N^{pro}$ of a pestivirus from a naturally occurring fusion protein or polyprotein. Examples of heterologous polypeptides are industrial enzymes (process enzymes) or polypeptides with pharmaceutical, in particular human pharmaceutical, activity.

Examples of preferred polypeptides with human pharmaceutical activity are cytokines such as interleukins, for example IL-6. Interferons such as leukocyte interferons, for example interferon α2B, growth factors, in particular haemopoietic or wound-healing growth factors, such as G-CSF, erythropoietin, or IGF, hormones such as human growth hormone (hGH), antibodies or vaccines.

In the process according to the invention the pestivirus is preferably selected from the group of CSFV, BDV and BVDV, with CSFV being particularly preferred.

Further preference is given to a process according to the present invention in which the first polypeptide of the fusion protein comprises the following amino acid sequence of the autoprotease $N^{pro}$ of CSFV (see also EMBL database accession number X87939) (amino acids 1 to 168, reading from N-terminal to the C-terminal direction) (SEQ ID NO. 1):
(1)-MELNHFELLYKTSKQKPVGVEEPVYDTAGR-
PLFGNPSEVHPQSTLKLPHDRGRGDIRTTLRDL
PRKGDCRSGNHLGPVSGIYIKPGPVYYQDY-
TGPVYHRAPLEFFDEAQFCEVTKRIGRVTGSDGKL-
YH IYVCVDGCILLKLAKRGTPRTLKWIRNFTNC-
PLWVTSC-(168), or the amino acid sequence of a derivative thereof with autoproteolytic activity.

A polypeptide exhibiting the autoproteolytic activity of an autoprotease $N^{pro}$ may also be a derivative of an autoprotease $N^{pro}$ of a pestivirus which is derived from this autoprotease $N^{pro}$ of a pestivirus by mutagenesis, in particular amino acid substitution, deletion, addition and/or amino acid insertion, as long as the required autoproteolytic activity, in particular for generating a desired heterologous polypeptide with homogeneous N-terminus, is retained. Methods for generating such derivatives by mutagenesis are familiar to the skilled person. It is possible by such mutations to optimize the activity of the autoprotease $N^{pro}$ in relation to different heterologous proteins to be cleaved from the fusion protein. After production of a nucleic acid which codes for a fusion protein which, besides the desired heterologous protein, comprises an autoprotease $N^{pro}$ derivative which exhibits one or more mutations by comparison with a naturally occurring autoprotease $N^{pro}$, it is established whether the required function is present by determining the autoproteolytic activity.

The autoproteolytic activity can be detected, for example, by initially solubilizing the isolated/purified IBs in 7 M guanldine/HCl solution and then diluting 1:100 in reaction solution. After incubation for about 24 h, the reaction solution is examined by SDS-PAGE for cleavage having taken place. A Western blot is carried out to identify the proportions processed and unprocessed. The proportion of cleaved material is determined by densitometric analysis of the Coomassie-stained SDS-PAGE gel.

A preferred process according to the present invention is, for example, one in which the expression vector comprises a nucleic acid molecule which codes for a fusion protein which has an N-terminal region in which one or more amino acids have been deleted or substituted in the region of amino acids 2 to 21 as long as the resulting derivative continues to exhibit the autocatalytic function of the autoprotease $N^{pro}$ to the desired extent. For the purpose of the present invention, autoprotease $N^{pro}$ derivatives which are preferred in the fusion protein comprise, for example, the amino acid sequence of the autoprotease N$^{pro}$ of CSFV with a deletion of amino acids 2 to 16 or 2 to 21. It is also possible by amino acid substitution or addition to exchange or introduce amino acid sequences, for example in order to introduce an amino acid sequence which assists purification.

A nucleic acid molecule which is particularly preferred in the process according to the present invention codes for a fusion protein in which the first polypeptide comprises the amino acid sequence Glu22 to Cys168 of the autoprotease N$^{pro}$ of CSFV or a derivative thereof with autoproteolytic activity, the first polypeptide furthermore having a Met as N-terminus, and the heterologous polypeptide being directly connected to the amino acid Cys168 of the autoprotease N$^{pro}$ of CSFV.

A nucleic acid molecule which is likewise preferred in the process according to the present invention codes for a fusion protein in which the first polypeptide comprises the amino add sequence Pro17 to Cys168 of the autoprotease N$^{pro}$ of CSFV or a derivative thereof with autoproteolytic activity, the first polypeptide furthermore having a Met as N-terminus, and the heterologous polypeptide being directly connected to the amino acid Cys168 of the autoprotease N$^{pro}$ of CSFV.

The said nucleic acid molecule is, in particular, in the form of a DNA molecule in the process according to the present invention.

An expression vector to be employed in the process according to the present invention preferably comprises at least one expression control sequence. Expression control sequences are, in particular, promoters (such as lac, tac, T3, T7, trp, gac, vhb, lambda pL or phoA), ribosome binding sites (for example natural ribosome binding sites which belong to the abovementioned promoters, cro or synthetic ribosome binding sites), or transcription terminators (for example rrnB T1T2 or bla). The above-mentioned host cell is preferably a bacterial cell of the genus Escherichia, in particular E. coli. However, it is also possible to use other bacterial cells (see below). In a preferred embodiment, the expression vector is a plasmid.

A bacterial host cell to be employed in the process according to the present invention can be selected, for example, from the group of the following microorganisms: Gram-negative bacteria such as Escherichia species, for example E. coli, or other Gram-negative bacteria, for example Pseudomonas sp., such as Pseudomonas aeruginosa, or Caulobacter sp., such as Caulobacter crescentus, or Gram-positive bacteria such as Bacillus sp., in particular Bacillus subtilis. E. coli is particularly preferred as host cell.

The bacterial host cell, i.e. the expression strain, is cultivated in accordance with microbiological practice known per se. The strain is generally brought up starting from a single colony on a nutrient medium, but it is also possible to employ cryopreserved cell suspensions (cell banks). The strain is generally cultivated in a multistage process in order to obtain sufficient biomass for further use.

On a small scale, this can take place in shaken flasks, it being possible in most cases to employ a complex medium (for example LB broth). However, it is also possible to use defined media (for example citrate medium). For the cultivation, a small-volume preculture of the host strain (inoculated with a single colony or with cell suspension from a cryoculture) is grown, the temperature for this cultivation not generally being critical for the later expression result, so that it is possible routinely to operate at relatively high temperatures (for example 30° C. or 37° C.). The main culture is set up in a larger volume (for example 500 ml), where it is in particular necessary to ensure good aeration (large volume of flask compared with the volume of contents, high speed of rotation). Since it is intended that expression take place in the form of insoluble inclusion bodies, the main culture will in most cases also be carried out at relatively high temperature (for example 30 or 37° C.). Inducible systems are particularly suitable for producing inclusion bodies (for example with trp, lac, tac or phoA promoter). After the late logarithmic phase has been reached (usually at an optical density of 0.5 to 1.0 in shaken flasks), in these cases the inducer substance (for example indoleacrylic acid, isopropyl β-D-thiogalactopyranoside=IPTG) is added and incubation is continued for 1 to 5 hours. During this time, most of the N$^{pro}$ fusion protein is deposited as inclusion bodies in the bacterial cytoplasm. The resulting cells can be harvested and processed further.

On a larger scale, the multistage system consists of a plurality of bioreactors (fermenters), it being preferred to employ defined nutrient media in this case in order to be able to improve the process engineering control of the process. In addition, it is possible greatly to increase biomass and product formation by metering in particular nutrients (fed batch). Otherwise, the process is analogous to the shaken flask. For example, a preliminary stage fermenter and a main stage fermenter are used, the cultivation temperature being chosen similar to that in the shaken flask. The preliminary stage fermenter is inoculated with a so-called inoculum which is generally grown from a single colony or a cryoculture in a shaken flask. Good aeration and a sufficient inducer concentration must also be ensured in the fermenter—and especially in the main stage thereof. The induction phase must, however, in some cases be made distinctly longer compared with the shaken flask. The resulting cells are once again delivered for further processing.

In the process according to the present invention, the inclusion bodies are isolated from the host cell in a known manner, as described, for example, in R. Rudolph et al., in: Creighton, T. E. (Ed.), Protein Function, A Practical Approach, IRL Press, (1996), 1–39; R. Rudolph, in: H. Tschesche (Ed.), Modern Methods in Protein and Nucleic Acid Research, De Gruyter, Berlin, (1990), 149–171; R. Rudolph, in: J. L Cleland & C. S. Craik (Eds.), Protein Engineering: Principles and Practices, Wiley-Liss Inc., (1995), 283–298.

For example, after the fermentation has taken place, the cells are harvested by centrifugation. The inclusion bodies (IBs) present therein can be obtained, after disruption of the cells, for example by means of high-pressure dispersion, by a simple centrifugation at low rotor speed. The purity in relation to the desired target protein can then be improved by multiple resuspension of the IBs in various buffers, for example in the presence of NaCl (for example 0.5–1.0 M) and/or detergent (for example Triton X-100). This usually leads to most of the foreign proteins in the IBs being removed. Any residual foreign proteins usually do not interfere with the autoproteolytic cleavage.

The solubilization routinely takes place by dissolving the IBs for example in a guanidine-containing buffer (for example 0.1 M tris/HCl, 6.0 M guanidine/HCl, 5 mM EDTA, 50 mM DTT) (see, for example, R. Rudolph et al., (1996); R. Rudolph (1990), R. Rudolph (1995), supra). After removal of insoluble material, for example by centrifugation, a protein determination can be carried out on the supernatant.

The autoproteolytic cleavage of the heterologous polypeptide from the fusion protein is achieved by diluting the solubilizate with a cleavage buffer (for example 1 ml of solubilizate+99 ml of cleavage buffer), for example with a tris-containing cleavage buffer, preferred concentration 0.8–1.0 M, or with an arginine-containing cleavage buffer, preferably with 0.4–0.6 M arginine, for example at a neutral pH, preferably pH 7.0–7.5, and at a temperature of, for example, less than 30° C., preferably 10–20° C., thus forming the reaction solution (see also R. Rudolph (1996), supra). The cleavage solution is subsequently incubated for a particular period, for example 12 h, and the extent of the $N^{pro}$ cleavage can be analysed by SDS-PAGE.

In a preferred embodiment, the solubilizate is diluted with an arginine-containing buffer so that the final concentration of arginine is up to 1.0 M, preferably 0.4–0.6 M. Alternatively, dilution is also possible by dialysing the solubilized inclusion bodies against an appropriate arginine-containing cleavage buffer.

The temperature of the reaction solution for the cleavage is, for example, between 0° C. and 30° C. The temperature can preferably be 10–20° C–20° C3.

The pH of the reaction solution is, for example, 5.0–9.0. The pH is preferably 7.0–8.0, in particular 7.0–7.5.

Where appropriate, the reaction solution contains DTT in a concentration of 0.5–100 mM. The DDT concentration is preferably about 5.5 mM.

The protein concentration in the reaction solution during the cleavage can be, for example, in the region of 20–150 μg/ml. The protein concentration is preferably less than 40 μg/ml.

The reaction solution can contain tris/HCl in a concentration of, for example, up to 1.0 M during the cleavage. The tris/HCl concentration is preferably between 0.8 M and 1.0 M.

Other buffer systems are also possible in place of arginine-containing and/or tris/HCl-containing buffers.

In a particularly preferred embodiment, the pH in the cleavage buffer is 7.0–7.5, the temperature during the cleavage is 16° C.–20° C., the protein concentration does not exceed 40–50 μg/ml, and the cleavage buffer contains about 5 mM DTT as reducing agent.

Finally, the heterologous polypeptide which has been cleaved from the fusion protein is isolated in a manner known per se (see, for example, M. P. Deutscher, in: Methods in Enzymology: Guide to Protein Purification, Academic Press Inc., (1990), 309–392).

The following examples illustrate the present invention, without in any way limiting the scope thereof.

EXAMPLES

Example 1

Expression and in vitro Cleavage of $N^{pro}$-hGH (Human Growth Hormone)

The fusion proteins are produced by heterologous expression in *Escherichia coli* in an expression system (vector p160TP1 with host W3110). All the elements in this system for constructing the vector originate from the *E. coli* genome.

p160TP1 is a pBR322-derived vector in which the expression is under the control of a modified *E. coli* trp promoter with deleted attenuator. The Shine-Dalgarno sequence of the attenuator peptide from the same operon is used as ribosome binding site (RBS). The double terminator T1T2 from the *E. coli* rmB gene ensures, together with the bla gene terminator which remains in the construct, efficient termination of the transcription. The expression cassette is inserted starting from the pBR322 EcoRI cleavage site in the counter-clockwise direction (i.e. contrary to the orientation of the tetracycline resistance gene). The β-lactamase gene (bla) is deleted together with the promoter. The structural genes for the heterologous proteins to be expressed are introduced (generally as PCR fragment cut to size) via the XbaI cleavage site at position 3506.

An expression plasmid (NPH-pET) serves as source of the $N^{pro}$-hGH structural gene. The plasmid comprises the known expression vector pET11a (F. W. Studier et al., Methods. Enzymol. 185 (1990), 60–89). Firstly a fusion protein composed of $N^{pro}$ and the CSFV nucleocapsid protein is cloned into the expression vector. This entails the first 16 amino acids of the natural $N^{pro}$ sequence (MELNHFELLYKTSKQK) (SEQ ID NO. 2) being replaced by a 10 amino acids-long oligo-histidine purification aid (MASHHHHHHH) (SEQ ID NO. 3). A SpeI cleavage site is introduced at the junction between $N^{pro}$ and nucleocapsid protein into the resulting expression plasmid by a targeted mutagenesis. This makes it possible to delete the structural gene for the nucleocapsid protein from the vector by restrictions with SpeI (at the 5' end) and XhoI (at the 3' end). The corresponding linearized $N^{pro}$-pET11a vector is removed by preparative gel electrophoresis from the nucleocapsid gene fragment. It is then possible to introduce the hGH structural gene via the "sticky" SpeI and XhoI ends.

For this purpose, the following preparatory work on the hGH gene is necessary. The structural gene is amplified from a cDNA bank from human brain, which can be processed (Clontech), using a high precision PCR (for example Pwo polymerase from Roche Biochemicals, procedure as stated by the manufacturer) The following oligonucleotides are employed for this purpose:

Oligonucleotide 1 ("N-terminal") (SEQ ID NO 4):

5'-ATAATTACTA GTTGTTTCCC AACCATTCCC TTATCCAGGC C-3'

Oligonucleotide 2 ("C-terminal") (SEQ ID NO 5):

5'-ATAATTGGAT CCTCGAGTTA TTAGAAGCCA CAGCTGCCCT CCAC-3'

A SpeI cleavage site is introduced at the 5' end, and an XhoI cleavage site is introduced at the 3' end via the oligonucleotide used. In addition, the double ochre stop codon (TAATAA) is introduced at the end of the structural gene for efficient termination of translation. The SpeI cleavage site at the front end permits ligation in reading frame with the $N^{pro}$-pET11a vector described above. The XhoI cleavage site at the rear end makes directed cloning-in possible. The plasmid produced in this way is named in NPH-pET.

This plasmid NPH-pET is that used, as already mentioned, as source of the structural gene of the $N^{pro}$-hGH fusion protein. For this purpose, once again a high-precision PCR with Pwo polymerase is employed using the plasmid NPH-pET linearized with XhoI as template. The following primers are used to produce a clonable fragment:

Front end (corresponding to the N-terminus of the protein) of the structural gene (SEQ ID NO. 6):

5'-AGGGTATCTA GAATTCTTATG CCAGTGGGAG TGGAG-GAACC G-3'

Rear end (corresponding to the C-terminus of the protein) of the structural gene (SEQ ID NO 7):

5'-AGAATTAAGC TTCTAGATTA TTAGAAGCCA CAGCTGCCCT CCAC-3'

The XbaI cleavage sites used subsequently for the cloning (front and rear) are shown underlined, and the start (ATG) and stop (TAATAA) codons are written in larger characters.

These two oligonucleotides result in amplification of a structural gene with an open reading frame (ORF) for a fusion protein (FP) in which the His₇ purification aid and the preceding amino acids (with the exception of the methionine necessary for the start of translation) have been completely deleted.

The sequence of the PCR fragment (1072 bp) which contains the open reading frame for the N$^{pro}$-hGH fusion protein is depicted below. The start codon and the two stop codons are printed in bold, and the XbaI cleavage sites used for the cloning are shown underlined (SEQ ID NO. 8).
5-AGGGTATCTAGAATTCTAJTCCAGTGGGAGTGGA-
GGAACCGGTGTATGACACCGCGGGGAGACC
ACTATTTGGGAACCCAAGTGAGGTACACCCACAAT-
CAACGCTGAAGCTGCCACACGACAGGGGGAGA-
GGAGATATCAGAACAACACTGAGGGACC-
TACCCAGGAAAGGTGACTGTAGGAGTGGCAAC-
CATCTAG GCCCGGTTAGTGGGATATACATAA-
AGCCCGGCCCTGTCTACTATCAGGACTACACGG-
GCCCAGTCTA TCACAGAGCTCCTTTAGAGT-
TCTTTGATGAGGCCCAGTTCTGCGAGGT-
GACTAAGAGAATAGGCAGG GTCACGGGTAG-
TGATGGTAACCTTTACCACATATATGTGTGCGT-
CGATGGTTGCATACTGCTGAAAT TAGCCAAA-
AGGGGCACACCCAGAACCCTAAAGTGGATTAGG-
AACTTCACCAACTCGTCCATTATGGGT AACTA-
GTTGTTTCCCAACCATTCCCTTATCCAGGCCT-
TTTGACAACGCTATGCTCCGCGCCCATCGT
CTGCACCAGCTGGCCTTTGACACCTACCAGGAG-
TTTGAAGAAGCCTATATCCCAAAGGAACAGAAGT
ATTCATTCCTGCAGAACCCCCAGACCTCCCTCTGTT-
TCTCAGAGTCTATTCCGACACCCTCCAACAG
GGAGGAAACACAACAGAAATCCAACCTAGAGCTG-
CTCCGCATCTCCCTGCTGCTCATCCAGTCGTGG-
CTGGAGCCCGTGCAGTTCCTCAGGAGTGT-
CTTCGCCAACAGCTGGTGTACGGCGCCTCT-
GACAGCA ACGTCTATGACCTCCTAAAGGAC-
CTAGAGGAAGGCATCCAAACGCTGATGG-
GGAGGCTGGAAGATGG CAGCCCCCGGACT-
GGGCAGATCTTCAAGCAGACCTACAGCAAGTTC-
GACACAAACTCACACAACGAT GACGCACTACT-
CAAGAACTACGGGCTGCTCTACTGCTTCAG- GAAG-
GACATGGACAAGGTCGAGACAT TCCTGCGCA-
TCGTGCAGTGCCGCTCTGTGGAGGGCAGCTGTG-
GCTTCTAATAATCTAGAAGCTTAAT TCT-3

This ORF thus codes for the fusion protein shown below, the proline at position two corresponding to the proline at position 17 of the natural N$^{pro}$ protein. The sequence of the N$^{pro}$ hGH fusion protein (344 amino acids, of which 153 N$^{pro}$ and 191 hGH) is thus as follows (read from the N-terminal to the C-terminal direction), with proline 17 (position 2 of the fusion protein) from the natural N$^{pro}$ sequence being shown in italics, and the hGH sequence being printed in bold (SEQ ID NO. 9).
MPVGVEEPVYDTAGRPLFGNPSEVHPQSTLK-
LPHDRGRGDiRTTLRDLPRKCDCRsGNHLGPVSGIY
IKPGPVYYQDYTGPVYHRAPLEFFDEAQFCE-
VTKRIGRVTGSDGKLYHIYVCVDGCILLKLAKRGTP
RTLKWIRNFTNCPLWVTSCFPTIPLSRpRDRAHRLU-
QLQEEEAYXPKEQKYSPLQNP DLTEGXQTLM-
GRLEDGSPRTGQDFQTYFNSHSDALRNYLLYC-
FRKDMDXVTZLRXVQC RSVEGSCGT The FP in the reduced state has an M$_r$ of 39 316.92 d, and the M$_r$ after a possible cleavage would be 17 220.02 d for the N$^{pro}$ part (reduced) and 22 114.88 d for the hGH part (reduced). N$^{pro}$ has six cysteines, and hGH four. In the bacterial cytoplasm these cysteines are likely to be in reduced form for the most part. During the subsequent processing there is presumably at least partial formation of disulfide bridges. It must be expected that the N-terminal methionine in the fusion protein (or the N$^{pro}$ part) will be mostly cleaved by the methionine aminopeptidase (MAP) intrinsic to the host, which would reduce the M$_r$ by, in each case, 131 d to 39 186 d (FP) and 17 089 d (N$^{pro}$) respectively.

The PCR fragment with the structural gene for the FP described is purified and cut with XbaI, and the two sought cleavage products are removed from the target fragment. This fragment is ligated to the expression vector p160TP1 as described.

For this purpose, the vector is initially linearized with XbaI and 5'-dephosphorylated with calf intestine phosphatase (CIP). T4 DNA ligase is used for ligation. The ligated DNA is introduced by electroporation into *Escherichia coli* K-12 DH10B and plated out on Luria broth (LB) agar plates with 15 mg/L tetracycline. Numerous clonal colonies result from this transformation. Plasmid DNA is isolated from several clones and examined by restriction analysis for the presence of an insert with the correct size and orientation. One clone is selected and subjected to detailed characterization by restriction analysis and DNA sequencing. The plasmid behaves in accordance with the calculations in all the investigations. This plasmid is called pNPH1 and is used for the subsequent work.

The sequence of the N$^{pro}$-hGH expression plasmid pNPH1 (4840 bp) is shown below. The start codon and the stop codon for the N$^{pro}$-hGH fusion protein are underlined. The open reading frame runs in the reverse direction when shown in this form (SEQ ID NO. 10).
5'-GAATTCTCATGTTTGACAGCTTATCATCGATAAG-
CTTTAATGCGGTAGTTTATCACAGTTAAAT
TGCTAACGCAGTCAGGCACCGTGTATGAAAT-
CTAACAATGCGCTCATCGTCATCCTCGGCACCGTCA
CCCTGGATCCTGTAGGCATAGGCTTGGTTATGCCG-
GTACTGCCGGcCCTCTTGCGGGATATCGTCCA
TTCCGACAGCATCGCCAGTCACTATGGCGTGCTGC-
TAGCGCTATATGCGTTGATGCAATTTCTATGC
GCACCCGTTCTCGGAGCACTGTCCGACCGCT- TTG-
GCCGCCGCCCAGTCCTGCTCGCTTCGCTACTTG
GAGCCACTATCGACTACGCGATCATGGCGACCA-
CACCCGTCCTGTGGATCCTCTACGCCGGACGCAT
CGTGGCCGGCATCACCGGCCGCCACAGGTGCGGTT-
GCTGGCGCCTATATCGCCGACATCACCGATGGG
GAAGATCGGGCTCGCCACTTCGGGCTCATGA-
GCGCTTGTTTCGGCGTGGGTATGGTGGCAG-
GCCCCG TGGCCGGGGGACTGTTGGGCGCCATCTC-
CTTGCATGCACCATTCCTTGCGGCGGCG-
GTGCTCAACGG CCTCAACCTACTACTGGGCTGC-
TTCCTAATGCAGGAGTCGCATAAGGGAGAGCGTCG-
A CCGATGCCC TTGAGAGCCTTCAACCCAGT-
CAGCTCCTTCCGCTGGGCGCGGGGCATGACTAT-
CGTCGCCGCACTTA TGACTGTCTTCTTTATC-
ATGCAACTCGTAGGACAGGTGCCGGCAGCGCTC-
TGGGTCATTTTCGGCGA GGACCGCTTTCGCTGGA-
GCGCGACGATGATCGGCCTGTCGCTTGCGGTAT-
TCGGAATCTTGCACGCC CTCGCTCAAGCCTTCGT-
CACTGGTCCCGCCACCAAACGTTTCGGC-
GAGAAGCAGGCCATTATCGCCG GCATGGCGGC-
CGACGCGCTGGGCTACGTCTTGCTGGCGTTCGC-
GACGCGAGGCTGGATGGCCTTCCC CATTATG-
ATTCTTCTCGCTTCCGGCGGCATCGGGATGCCCGC-
GTTGCAGGCCATGCTGTCCAGGCAG GTAGATG-
ACGACCATCAGGGACAGCTTCAAGGATCGCTGC-
GGCTCTTACCAGCCTAACTTCGATCA CTGGACC-
GCTGATCGTCACGGCGATTTATGCCGCCTCGGC-
GAGCACATGGAACCGGTTGGCATGGAT TGTAG- GCGCCGCCCTATACCTTGTCTGCCTCCCCCCG-
TTGCGTCGCGGTGCATGGAGCCGGGCCACC-
TCGACCTGAATGGAAGCCGGCGGCACCTCGCT-
AACGGATTCACCACTCCAAGAATTGGAGCCAATCA
ATTCTTGCGGAGAACTGTGAATGCGCAAACCA-
ACCCTTGGCAGAACATATCCATCGCGTCCGCCATC-
TCCAGCAGCCGCACGCGGCGCATCTCGGG-
CAGCGTTGGGTCCTGGCCACGGGTGCGCA-
TGATCGTGC TCCTGTCGTTGAGGACCCGGCTAG-
GCTGGCGGGGTTGCCTTACTGGTTACCA-
GAATGAATCACCGAT ACGCGAGCGAACGTG-
AAGCGACTGCTGCTGCAAAACGTCTGCGACCTGA-
GCAACAACATGAATGGTC TTCGGTTTCCGT-
GTTTCGTAAAGTCTGGAAACGCGGAAGT-
CAGCGCCCTCCACCATTATGTTCCGGA TCTGCAT-
CGCAGGATGCTGCTGGCTACCCTGTGGAACAC-
CTACATCTGTATTAACGAAGCGCTGGCA TTG-
ACCCTGAGTGATTTTCTCTCGTCCGCCGCA-
TCCATACCGCCAGTTGTTTACCCTCACAACGT-
TCCAGTAACCGGGCATGTTCATCATCAGTAAC-
CCGTATCGTGAGCATCCTCTCTCGTTTCATCGGTA
TCATTACCCCCATGAACAGAAATTCCCCCTTAC-
ACGGAGGCATCAAGTGACCAAACAGGAAAAACC-
GCCCTTAACATGGCCCGCTTTATCAGAAGCCAGA-
CATTAACGCTTCTGGAGAAACTCAACGAGCTGG-
ACGCGGAT CAGGCAGACATCTGTGAATCGCTTCA-
CGACCACGCTGATGAGCTTTACCGCAGCTG-
CCTCGCGCGTTTCGGTGATGACGGTGAAAAC-
CTCTGACACATGCAGCTCCCGGAGACGGT-
CACAGCT TGTCTGTAAGCGGATGCCGGAGC-
AGACAAGCCCGTCAGGCCGTCAGCGGGTGTT-
GGCGGGTGTC GGGGCGCAGCCATGACC-
CAGTCACGTAGCGATAGCGGAGTGTATACTGGCT-
TAACTATGCGGCATCA GAGCAGATTGTACT-
GAGAGTGCACCATATGCGG TACCGCACAGATGCG-
TAAGGACAAAAT ACCGCATCAGGCGCTCTTC-
CGCTTCCTCGCTCACTGACTCGCTGCGCTCGGTCG-
TTCGGCTGCGGCG AGCGGTATCAGCTCACTCA-
AAGGCGGTAATACGGTTATCCACAGAATCAGGG-
GATAACGCAGGAAAG AACATGTGAGCAAAAGGC-
CAGCAAAAGGCCAGGAACCGTAAAAAG-
GCCGCGTTGCTGGCGTTTTTCC ATAGGCTC-
CGCCCCCCTGACGAGCATCACAAAAATC-
GACGCTCAAGTCAGAGGTGGCGAAACCCGAC
AGGACTATAAAGATACCAGGCGTTTCCCCCTG-
GAAGCTCCCTCGTGCGCTCTCCTGTTCCGACCCTG-
CCGCTTACCCGATACCTGTCCGCCTTTCTCCCT-
TCGGGAAGCGTGGCGCTTTCTCATAGCTCACGCT
GTAGGTATCTCAGTTCGGTGTAGGTCGTTCGCTC-
CAAGCTGGGCTGTGTGCACGAACCCCCCGTTCA
GCCCGACCGCTGCGCCTTATCCGGTAACTATCGTCT-
TGAGTCCAACCCGGTAAGACACGACTTATCG-
CCACTGGCAGCAGCCACTGGTAACAGGATTA-
GCAGAGCGAGGTATGTAGGCGGTGCTACAGAGT-
TCT TGAAGTGGTGGCCTAACTACGGCTACACTAG-
AAGGACAGTATTTGGTATCTGCGCTCTGC-
TGAAGCC AGTTACCTTCGGAAAAAGAGTTGGTA-
GCTCTTGATCCGGCAAACAAACCACCGCTG-
GTAGCGGTGGT TTTTTTGTTTGCAAGCACCAGAT-
TACGCGCAGAAAAAAGGATCTCAAGAA-
GATCCTTTGATCTTTT CTACGGGGTCT-
GACGCTCAGTGGAACGAAAACTCACGTTAAG-
GGATTTTGGTCATGAGATTATCAAA AAGGATCT-
TCACCTAGATCCTTTTAAATTAAAAATGAAGTTT-
TAAATCAATCTAAAGTATATATGAG TAAACTTGG-
TCTGACAGTTACCTCGAGGCCATCCGTCAGGATG-
GCCTTCTGCTTAATTTGATGCCTG GCAGTTTATG-
GCGGGCGTCCTGCCCCCCACCCTCCGGGCCG-
TTGCTTCGCAACGTTCAAATCCGCTC CCGGCGG-
ATTTGTCCTACTCAGGAGAGCGTTCACCGACAAAC-
AACAGATAAAACCAAAGGCCCAGTCTTTCOA-
CTGAGCCTTTCGTTTTATTCTAGATTATTAGAAGC-
CACAGCTGCCCTCCACAGAGCGGCAC TGCACG-
ATGCGCAGGAATGTCTCGACCTTGTCCATGTCCT-
TCCTGAAGCAGTAGAGCAGCCCGTAGT TCTT-
GAGTAGTGCGTCATCGTTGTGTGAGTTTGTGTCG-
AACTTGCTGTAGGTCTGCTTGAAGATCTG-
CCCAGTCCGGGGGCTGCCATCTTCCAGCCTCCCCA-
TCAGCGTTTGGATGCCTTCCTCTAGGTCCTTT
AGGAGGTCATAGACGTTGCTGTCAGAGGC-
GCCGTACACCAGGCTGTTGGCGAAGACACTCCTGA-
GGA ACTGCACGGGCTCCAGCCACGACTGGATG-
AGCAG- CAGGGAGGATGCGGAGCAGCTCTAGGT-
TGGATTT CTGTTGTGTTTCCTCCCTGT-
TGGAGGGTGTCGGAATAGACTCTGAGAAA-
CAGAGGGAGGTCTGGGGG TTCTGCAGGA-
ATWATACTTCTGTTCCTTTGGGATATAGGCTTC-
TTCAAACTCCTGGTAGGTGTCAA AGGCCAGCTG-
GTGCAGACGATGGGCGCGGAGCATAGCGTTG-
TCAAAAGGCCTGGATAAGGGAATGGT TGGGAA-
ACAACTAGTTACCCATAATGGACAGTTGGTG-
AAGTTCCTAATCCACTTTAGGGTTCTGGGT
GTGCCCCTTTGGCTAATTTCAGCAGTATGCAACCAT-
CGACGCACACATATATGTGGTAAAGCTTAC
CATCACTACCCGTGACCCTGCCTATTCTCTTAGT-
CACCTCGCAGAACTGGGCCTCATCAAAGAACTC
TAAAGGAGCTCTGTGATAGACTGGGCCCGTGT-
AGTCCTGATAGTAGACAGGGCCGGGCTTTATGTAT
ATCCCACTAACCGGGCCTAGATGGTTGC-
CACTCCTACAGTCACCTTTCCTGGGTAG-
GTCCCTCAGTG TTGTTCTGATATCTCCTCTC-
CCCCTG TCGTGTGGCAGCTTCAGCGTT-
GATTGTGGGTGTACCTCACT TGGGTTCCCAAAT-
AGTGGTCTCCCCGCGGTGTCATACACCG-
GTTCCTCCACTCCCACTGGCATAGAA TTCTAGA-
TACCCTTTTTACGTGAACTTGCGTACTAGTTAAC-
TAGTTCGATGATTAATTGTCAACAGC TCATTTC-
AGAATATTTGCCAGAACCGTTATGATGTCGGCGC-
AAAAAACATTATCCAGAACGGGAGTG CGCCTT-
GAGCGACACGAATTATGCAGTGATTTACGACCT-
GCACAGCCATACCACAGCTTCCGAWGG CT-
GCCTGACGCCAGAAGCATTGGTGCACCGTGCACTC-
GAGATGCGCGTCGGCACCTGGCGATCACC The *Escherichia coli* host strain for expressing the N$^{pro}$-hGH fusion protein is selected on the basis of considerations of productivity and biological safety. *Escherichia coli* K-12 is the best-characterized line of the species *E. coli* (B. J. Bachmann; in: J. L Ingraham et al., (Ed.) *Escherichia coli and Salmonella typhimurium*: cellular and molecular biology. American Society for Microbiology, Washington D.C. (1987a), pp. 1191–1219; B. J. Bachmann 1987b; Barbara J. (1987b) Linkage map of *Escherichia coli* K-12, edition 7. In: *Escherichia coli and Salmonella typhimurium*, Vol. 2. Ed.: F. C. Neidhard. Am. Soc. Microbiol., Washington D.C. (1987b), 807–876; K. F. Jensen, *J. Bacteriol.* 175 (1993), 3401–3407) and its representatives are generally regarded as safe.

*Escherichia coli* K-12 W3110 (ATCC 27325) is a prototropic derivative, which is very dose to the wild type, of *Escherichia coli* K-12 and is frequently employed as host strain for expressing heterologous proteins. It has been deposited at the American Type Culture Collection (ATCC) and has the following genotype:
[F mcrA mcrB IN(rrnD-rrnE)1 lambda]

The strain can be purchased from the ATCC. Its growth is excellent on fully synthetic media without complex nitrogen sources and process engineering control thereof it possible very effectively.

The expression strain W3110[pNPH1] is produced by transformation of the expression plasmid pNPH1 described above into W3110. The transformation takes place by electroporation, using 10% glycerol as suspending medium. 50 ng (1 μL) of a pNPH1 solution in water were mixed with 30 μL of a W3110 cell suspension and exposed to an 1800 V pulse in a 1 mm cuvette (Eppendorf Electroporator 2510). The cells are resuspended in SOC medium, shaken at 37° C. for 1 h and then plated out on Luria broth agar plates with 15 mg/L tetracycline. Numerous clones result from this transformation after incubation at 37° C. (over night).

A medium-sized colony with distinct margins is picked and forms the basis for the expression strain W3110 [pNPH1]. The clone is cultivated and preserved in cryoampoules at −80° C. (master cell bank MCB). For daily use, the strain is streaked on LB-tetracycline agar plates.

The strain W3110[pNPH1] is subcultured from a single colony on an agar plate and this is used to inoculate a preculture in Luria broth +15 mg/L tetracycline (200 mL in a 1 L baffle flask). The preculture is shaken at 250 rpm at 30° C. for 14 h and, during this, reaches an $OD_{600}$ of about 1.0. 10 mL portions of preculture are then used to inoculate the main cultures (in each case 330 mL of citrate medium in 1 L baffle flasks) (3% inoculum). The main cultures are grown at 37° C. (250 rpm) until the $OD_{600}$ is 0.8 and then production of the fusion protein is induced with 50 μg of indoleacrylic acid per mL of culture (final concentration; stock solution 5 mg/mL in 100% analytical grade EtOH). The cultures are cultivated further at 37° C. and 250 rpm for 4 h, during which the $OD_{600}$ reaches about 1.5 to 3.0.

The cultures are transferred into sterile 500 mL centrifuge bottles and centrifuged at 10,000 g for 30 min. The centrifugation supernatant is completely discarded, and the pellets are frozen at −80° C. until processed further.

About 12 g (wet weight) of BL12 1(DE3) cell pellet are then suspended in 30 mL of 50 mM tris/HCl, 5 mM benzamidine, pH 8.0 and homogenized using an Ultraturrax. After addition of 0.5 mM EDTA and 0.1% (w/v) lysozyme, the cell suspension is incubated in an ice bath for 30 min. Subsequent ultrasound treatment (7×20 sec with 20 sec pause in each case) leads to a complete disruption of the cells. Then 10 mM $MgCl_2$ and 0.006% (w/v) DNase are added to the disrupted suspension and incubated at 4° C. for 30 min. Insoluble and soluble constituents are subsequently separated by centrifugation (JA 20; 7700 g). The pellet is suspended in 40 mL of 50 mM tris/HCl, 5 mM benzamidine, 5 mM EDTA, pH 8.0 and again centrifuged (JA 20; 7700 g). This step is repeated twice more, and the resulting pellets are suspended in 40 mL of 20 mM tris/HCl, pH 7.0. 20 mL of 1.5 M NaCl, 60 mM EDTA, pH 7.0 are added to the suspension and incubated in an ice bath for 30 min. Finally, a further centrifugation (JA 20; 7700 g) and an $H_2O$ washing step are carried out. The resulting pellet represents the $N^{pro}$-hGH IB (inclusion body) material.

This is routinely followed by suspending about 100 mg of IB material in 2 mL of 6.0 M guanidine hydrochloride, 0.1 M tris, 5 mM EDTA, 50 mM DTT, pH 9.0 at RT for 30 min. Insoluble constituents are subsequently removed by centrifugation (10 min/30000 g). A protein determination is carried out on this supernatant (protein concentration about 20 mg/mL). The solubilizate produced in this way is either immediately employed in cleavage tests or stored at −20° C. (max. 7 days).

Example 2

Cleavage of the Inclusion Body Fusion Proteins Under Various Conditions

Cleavage of the $N^{pro}$ portion is made possible in principle by a 1:100 (or larger) dilution of the solubilizate (see above) in cleavage buffer (residual concentration of guanidine hydrochloride ≦0.06 M). The protein concentration during this is routinely 20 μg/mL (in cases of exception, this is pointed out hereinafter).

It is furthermore possible to achieve cleavage of the $N^{pro}$ portion by dialysis (1:100) of the solubilized material against cleavage buffer.

The extent of the cleavage of the $N^{pro}$ portion can be measured by detecting the cleavage products after SDS-PAGE. This entails the polyacrylamide gels being photographed after SDS-PAGE has taken place, and the intensity of the appropriate bands being measured. The appropriate bands are identified by Western blot in preliminary tests.

Example 2.1

In vitro Cleavage of $N^{pro}$-hGH by Arginine

The cleavage takes place by dilution (1:100) of the solubilizate in cleavage buffer (20 mM tris/HCl, 2 mM EDTA, 5 mM DTT, pH 7.0 and the particular arginine concentrations) at RT. The protein concentration in the cleavage mixtures is 20 μg/mL. The extent of the cleavage is measured after 24 h by detecting the cleavage products after SDS-PAGE.

It emerges that the $N^{pro}$ cleavage efficiency can be distinctly increased by adding arginine in the cleavage buffer. Maximum cleavage takes place at a concentration of 0.4–0.6 M arginine.

Example 2.2

Cleavage of $N^{pro}$ from $N^{pro}$-hGH by Arginine at Various Temperatures

The cleavage takes place by dilution (1:100) of the solubilizate in cleavage buffer (20 mM tris/HCl, 2 mM EDTA, 5 mM DTT, pH 7.0, 0–1.0 M arginine) at the particular temperatures. The protein concentration in the cleavage mixture is 20 μg/mL. The extent of the cleavage is measured after 24 h by detection of the cleavage products after SDS-PAGE.

It emerges that a maximum cleavage lakes place at temperatures between 10 and 20° C.

Example 2.3

Extent of the Cleavage of $N^{pro}$ from $N^{pro}$-hGH as a Function of the pH at Various Temperatures The cleavage takes place by dilution (1:100) of the solubilizate in cleavage buffer (20 mM tris/HCl, 2 mM EDTA, 5 mM DTT, 0.5 M arginine) at the particular pH. The protein concentration in the cleavage mixture is 20 μg/mL. The extent of the cleavage was measured after 24 h by detecting the cleavage products after SDS-PAGE.

A systematic variation of the pH in the cleavage buffer form pH 5.0 to 9.0 is carried out. With the arginine concentration employed, a pH of 7.0–7.5 is optimal for cleavage of the $N^{pro}$ fusion protein.

Example 2.4

Cleavage of $N^{pro}$ from $N^{pro}$-hGH at Various DTT Concentrations

The dependence of the cleavage efficiency on the DTT concentration is investigated.

The cleavage takes place by dilution (1:100) of the solubilizate in cleavage buffer (20 mM tris/HCl, 2 mM EDTA, pH 7.0, 0.5 M arginine, 0–100 mM DTT at 15° C.). Because of the DTT concentration in the solubilizate, the mixture with "0 mM DTT" still contains 0.5 mM DTT. The protein concentration in the cleavage mixture is 20 µg/mL. The extent of the cleavage is measured after 24 h by detecting the cleavage products after SDS-PAGE.

A maximum cleavage of the $N^{pro}$ portion is reached at about 5.5 mM DTT.

Example 2.5

Variation of the pH in Solubilizate for Cleavage of $N^{pro}$-hGH

The cleavage takes place by dilution (1:100) of the solubilizate at various pH values (pH 6.0, pH 7.0, pH 8.0, pH 9.0) in the cleavage buffer (20 mM tris/HCl, 2 mM EDTA, 5 mM DTT, pH 7.0, 0–0.8 M arginine at 15° C.). The pH values are adjusted by titrating the solubilization buffer to the appropriate pH values before mixing with the IBs. The protein concentration in the cleavage mixture is 20 µg/mL. The extent of the cleavage is measured after 24 h by detecting the cleavage products after SDS-PAGE.

it emerges that a pH of 7.0–8.0 in the solubilizate is optimal.

Example 2.6

Kinetics of $N^{pro}$ Cleavage from $N^{pro}$-hGH

Reactivation of denatured $N^{pro}$-hGH is started by dilution (1:100) in 20 mM tris/HCl, 0.5 M arginine, 2 mM EDTA, 10 mM DTT, pH 7.0 at 15° C.

It emerges that the and point of the cleavage is reached after about 24 h.

Example 2.7

Cleavage of $N^{pro}$ from $N^{pro}$-hGH by Dilution at Various Protein Concentrations The cleavage takes place by dilution (1:100) of the solubilizate in cleavage buffer (20 mM tris/HCl, 0.5 M arginine, 2 mM EDTA, 10 mM DTT, pH 7.0 at 15° C.). A check is carried out to determine whether the cleavage has taken place after about 24 h by detection of the cleavage products after SDS-PAGE.

It emerges that protein concentrations ≧40 µg/mL lead to a distinct decline in the cleavage efficiency. Further tests reveal that the optimal protein concentration is 20–40 µg/ml.

Example 2.8

$N^{pro}$ Cleavage from $N^{pro}$-hGH by Dialysis as a Function of the Protein Concentration Guanidine hydrochloride is removed from solubilized $N^{pro}$-hGH IB material by dialysis (1:100) against 20 mM tris/HCl, 0.5 M arginine, 2 mM EDTA, 10 mM DTT, pH 7.0 at 4° C., and thus the cleavage is initiated. After about 24 h, SDS-PAGE is used to analyse for $N^{pro}$ cleavage having taken place. It emerges that cleavage of the $N^{pro}$ portion can be achieved not only by dilution but also by dialysis of the solubilized material.

Example 2.9

Efficiency of Cleavage of $N^{pro}$ from $N^{pro}$-hGH as a Function of the tris/HCl Concentration The cleavage takes place by dilution (1:100) of the solubilizate in cleavage buffer (2 mM EDTA, 20 mM DTT, pH 7.0, 0.1–1.0 M tris/HCl at 15° C.). The cleavage was checked after about 24 h by detecting the cleavage products after SDS-PAGE.

It emerges that an increasing tris/HCl concentration up to 0.8 M in the buffer improves the $N^{pro}$ fusion protein cleavage yield. An increase above this causes no measurable enhancement of the $N^{pro}$ cleavage.

The reaction ought thus preferably to take place at tris/HCl concentrations of 0.8–1.0 M.

Example 3

Expression and in vitro Cleavage of $N^{pro}$-pGH (Porcine Growth Hormone)

Production of the $N^{pro}$-pGH expression vector starts from pNPH1 (see Example 1). The plasmid is linearized with BgIII and amplified by means of PCR. This entails the entire plasmid apart from the region of the hGH structural gene (from the codon for Phe 1 to the codon for Phe 191) being amplified with Pwo polymerase and primers without 5'-phosphate. The purified PCR fragment is employed as vector in the ligation with the pGH structural gene. Removal of 5'-phosphates (for example using calf intestine phosphatase, Arctic shrimp alkaline phosphatase) prevents circularization by self-ligation.

The pGH structural gene is likewise produced by PCR amplification. The template used is a porcine cDNA bank (for example porcine liver 5'-stretch cDNA library from Clontech or porcine brain or pituitary cDNA bank). The following primers are used for the amplification, and are in each case provided with a 5'-phosphate during the synthesis:

Front end (corresponding to the N-terminus of the protein) of the structural gene (Phe1 to Ser7) (SEQ ID NO. 11):

5'-TTC CCA GCC ATG CCC TTG TCC -3'

Rear end (corresponding to the C-terminus of the protein) of the structural gene (Phe190 to Val184) (SEQ ID NO. 12):

5'-GAA GGC ACA GCT GCT CTC CAC-3'

The PCR fragment contains exclusively the ORF (structural gene) for mature pGH. Ligation (T4 DNA ligase) results in an ORF for $N^{pro}$-pGH which is analogous to that of pNPH1. The fusion protein described hereinafter is encoded by this ORF. The ligated DNA is introduced by electroporation in *Escherichia coli* K-12 DH10B (electrocompetent cells supplied by Life Technologies, genotype *Escherichia coli* K-12 F⁻ mcrA Δ(mrr-hsdRMS-mcrBC) φB01acZΔM15 ΔlacX74 deoR recA1 endA1 araD139 Δ(ara, leu)7697 galU galK λ-rpsl. nupG) and plated out on Luria broth (LB) agar plates with 15 mg/L tetracycline. This transformation results in numerous clonal colonies. The plasmid DNA is isolated from several clones and examined by a restriction analysis for the presence of an insert with the correct size and orientation. One clone is selected and subjected to detailed characterization by restriction analysis and DNA sequencing. The plasmid behaves in accordance with calculations in all the investigations. This plasmid is called pNPP1 and used for the subsequent work.

In the following amino acid sequence (read from the N-terminal to the C-terminal direction) of the $N^{pro}$-pGH fusion protein (342 amino acids, of which 153 are $N^{pro}$ and 189 are pGH), proline 17 (position 2 fusion protein) from the natural $N^{pro}$ sequence is put in italics, and pGH sequence is shown in bold print (SEQ ID NO. 13).

MPVGVEEPVYDTAGRPLFGNPSEVHPQSTLKLP-HDRGRGD*i*RTTLRDLPRKGDCRSGNHLGPVSG*i*Y*i*KPGPVYYQDYTGPVYHRAPLEFFDFAQFCEVTYRi-

GRVTGSDGKLYHiYVCVDGCiLLKLAKRGTP RTLK-WiRNFTWCPLWVTSCYPAMPLSSL ARAVLRAQME-QLAADTYKEFERAYXPEGQRY8SXQAQ VESOCAF

The FP in the reduced state has an $M_r$ of 38 819.82 d, and the $M_r$ after a possible cleavage would be 17 220.02 d for the $N^{pro}$ part (reduced) and 21 617.79 d for the pGH part (reduced). $N^{pro}$ has six cysteines, and pGH four. In the bacterial cytoplasm these cysteines are likely to be in reduced form for the most part. During the subsequent processing there is presumably at least partial formation of disulfide bridges. It must be expected that the N-terminal methionine in the fusion protein (or the $N^{pro}$ part) will be mostly cleaved by the methionine aminopeptidase (MAP) intrinsic to the host, which would reduce the $M_r$ by, in each case, 131 d to 38 689 d (FP) and 17 089 d ($N^{pro}$) respectively.

The expression strain W3110[pNPP1] is produced as described in Example 1 by transformation (electroporation) of the expression plasmid pNPP1 in *Escherichia coli* K-12 W3110. In this case too, even detailed characterization revealed no deviations from the expected restriction pattern.

A medium-sized colony with distinct margins is picked from the transformation plate and forms the basis for the expression strain W3110[pNPP1]. The clone is cultivated and preserved in cryoampoules at −80° C. (master cell bank MCB). The strain is streaked on LB-tetracycline agar plates for daily use.

Expression of the $N^{pro}$-pGH fusion protein takes place as described in Example 1 for the $N^{pro}$-hGH fusion protein.

Preparation of the $N^{pro}$-pGH IBs takes place as described in Example 1 for a $N^{pro}$-hGH fusion protein.

Example 4

In-vitro Cleavage of $N^{pro}$ from $N^{pro}$-pGH

Solubilization and renaturation tests corresponding to those described above for $N^{pro}$-hGH are carried out for the $N^{pro}$-pGH fusion protein. After variation of the parameters already described (see above) it emerges that in-vitro cleavage of the $N^{pro}$ portion is possible after solubilization and renaturation also in the case of the $N^{pro}$-pGH fusion protein.

What is claimed is:

1. A process for the recombinant production of a heterologous polypeptide, comprising,
   (i) cultivation of a bacterial host cell which is transformed with an expression vector which comprises a nucleic acid molecule which codes for a fusion protein, the fusion protein comprising a first polypeptide which exhibits the autoproteolytic function of an autoprotease $N^{pro}$ of a pestivirus, and a second polypeptide which is connected to the first polypeptide at the C-terminus of the first polypeptide in a manner such that the second polypeptide is capable of being cleaved from the fusion protein by the autoproteolytic activity of the first polypeptide, and the second polypeptide being a heterologous polypeptide, wherein cultivation occurs under conditions which cause expression of the fusion protein and formation of corresponding cytoplasmic inclusion bodies,
   (ii) isolation of the inclusion bodies from the host cell,
   (iii) solubilization of the isolated inclusion bodies,
   (iv) dilution of the solubilizate to give a reaction solution in which the autoproteolytic cleavage of the heterologous polypeptide from the fusion protein is performed, and
   (v) isolation of the cleaved heterologous polypeptide.

2. The process according to claim 1, wherein the pestivirus is selected from the group of CSFV, BDV and BVDV.

3. The process according to claim 2, wherein the pestivirus is CSFV.

4. A process of claim 1, wherein the nucleic acid molecule is a DNA molecule.

5. The process of claim 1, wherein the expression vector is a plasmid.

6. The process of claim 1, wherein the bacterial host cell is an *E. coli* cell.

7. The process of claim 3, wherein the first polypeptide comprises the amino acid sequence:
   (1)-
   MELNHFELLYKTSKQKPVGVEEPVYDTAGRPLF-
   GNPSEVHPQSTLKLPHDRGRGDIRTTLR
   DLPRKGDCRSGNHLGPVSGIYIKPGPVYY-
   QDYTGPVYHRAPLEFFDEAQFCEVTKRI-
   GRVTGS DGKLYHIYVCVDGCILLKLA-
   KRGTPRTLKWIRNFTNCPLWVTSC-(168) (SEQ ID NO:1).

8. The process of claim 3, wherein the first polypeptide comprises the amino acid sequence Glu22 to Cys168 of the autoprotease $N^{pro}$ of CSFV (SEQ ID NO:1), wherein the first polypeptide has a Met as N-terminus, and wherein the heterologous polypeptide is directly connected to the amino acid Cys168 of the autoprotease $N^{pro}$ of CSFV.

9. The process of claim 3, wherein the first polypeptide comprises the amino acid sequence Pro17 to Cys168 of the autoprotease $N^{pro}$ of CSFV (SEQ ID NO:1), wherein the first polypeptide has a Met as N-terminus, and wherein the heterologous polypeptide is connected to the amino acid Cys168 of the autoprotease $N^{pro}$ of CSFV.

* * * * *